United States Patent [19]

Zarnowski et al.

[11] Patent Number: 4,955,325
[45] Date of Patent: Sep. 11, 1990

[54] ACETABULAR CUP COMPONENT CEMENT SPACER SYSTEM

[75] Inventors: Alfred J. Zarnowski, North Plainfield; Robert C. Cohen, Rockaway Township, Morris County, both of N.J.

[73] Assignee: Osteonics Corp., Allendale, N.J.

[21] Appl. No.: 365,791

[22] Filed: Jun. 14, 1989

[51] Int. Cl.⁵ .............................................. A61F 2/34
[52] U.S. Cl. .................................... 623/22; 623/18
[58] Field of Search ................ 623/16, 17, 18, 19, 623/20, 21, 22, 23; 128/927

[56] References Cited

U.S. PATENT DOCUMENTS

| | | | |
|---|---|---|---|
| 4,293,962 | 10/1981 | Fuson | 623/16 |
| 4,563,778 | 1/1986 | Roche et al. | 623/16 |
| 4,566,138 | 1/1986 | Lewis et al. | 623/16 |

FOREIGN PATENT DOCUMENTS 3310944  10/1984  Fed. Rep. of Germany ........ 623/23

Primary Examiner—David J. Isabella
Attorney, Agent, or Firm—Samuelson & Jacob

[57] ABSTRACT

A cement spacer system for interoperatively converting an acetabular cup component of the type constructed for cementless affixation to a construction suitable for cemented affixation includes a plurality of cement spacers associated with a spacer inserter for selectively inserting the cement spacers into the wall of the acetabular cup component, during the implant procedure, to provide the acetabular cup component with cement spacers suitable for cemented affixation of the acetabular cup component.

9 Claims, 4 Drawing Sheets

ACETABULAR CUP COMPONENT CEMENT SPACER SYSTEM

The present invention relates generally to the implant of acetabular cup components of hip joint prostheses and pertains, more specifically, to a system which permits an interoperative choice between cementless affixation and cemented affixation utilizing an acetabular cup component selected at the outset of the implant procedure.

The replacement of the natural hip joint with an implanted hip prosthesis is becoming more commonplace as technological advances continue to simplify medical procedures, thereby facilitating the treatment of many more cases where such procedures heretofore have been impractical, if not impossible. Replacement of the natural hip joint often requires the implant of an acetabular cup component to provide a deteriorated acetabulum with an appropriate bearing member for the replacement prosthesis. The affixation of an acetabular cup component within the natural hip bone, or ilium, usually is accomplished either with a suitable cement or with known cementless arrangements.

Often, the surgeon cannot be certain as to which affixation arrangement would best be suited to a particular patient until during the course of the actual implant operation, when the hip joint is exposed for direct examination by the surgeon. Thus, it may become necessary for the surgeon to have on hand, during the procedure, more than one acetabular cup component so as to enable the appropriate choice. The necessity for maintaining available a plurality of acetabular cup components for a single procedure is wasteful and expensive, as well as time-consuming during a procedure which should be accomplished within the shortest time consistent with the attainment of the desired result.

The present invention provides a system which enables a single chosen acetabular cup component of essentially conventional configuration to be affixed either with or without cement so that a surgeon may select the method of affixation interoperatively, without the necessity for having available multiple acetabular cup components during the actual implant procedure. In this connection, the present invention has several objects and advantages, some of which may be summarized as follows: Simplifies the procedure and reduces the time necessary for accomplishing the implant of an acetabular cup component, while reducing the cost, in that a single selected acetabular cup component may be implanted with either cementless or cemented affixation, with the choice being made available during the actual implant procedure; enables selection of the most appropriate affixation mechanism interoperatively so as to assure that the preferred mechanism is utilized for maximum effectiveness at reduced risk and at lessened expense; reduces hospital inventory and simplifies preoperative selection of an appropriate acetabular cup component; enhances patient safety and comfort in that optimum affixation is made available with reduced risk; provides the surgeon with the ability to optimize the implant of a prosthetic hip joint with less time and with increased ease.

The above objects and advantages, as well as further objects and advantages, are attained by the present invention which may be described briefly as a cement spacer system for use in connection with an acetabular cup component including a shell-like wall having an outer affixation surface for direct affixation of the acetabular cup component to the bone of the acetabulum and apertures passing through the wall at locations spaced apart along the outer affixation surface, each aperture having an inner rim-like portion of given inside diameter, a cement spacer system enabling selective interoperative conversion of the acetabular cup component for cemented affixation of the acetabular cup component to the bone of the acetabulum, the cement spacer system comprising: a plurality of cement spacers, each cement spacer including a spacer head having an axial spacing length, and confronting locking shoulders adjacent the spacer head and having an overall diameter greater than the inside diameter of the rim-like portion of a respective aperture in the wall of the acetabular cup component, a generally annular groove essentially complementary to the inside diameter of the rim-like portion of the corresponding aperture and interposed between the confronting locking shoulders, and resilient deflection means for enabling lateral resilient deflection of the locking shoulders to admit the rim-like portion of the corresponding aperture between the confronting locking shoulders in response to axial insertion of the cement spacer into the respective aperture, and a bore passing axially through the cement spacer; and a spacer inserter including a gripping handle, a locator rod extending axially from the handle and having a rod diameter complementary to the axial bore of each cement spacer such that the cement spacers may be strung along the locator rod, a lateral pushing surface placed axially between the handle and the locator rod for engaging the confronting adjacent cement spacer strung upon the locator rod such that upon axial pushing of the handle, axial force is transmitted to the cement spacers strung upon the locator rod for insertion and securement of each cement spacer within a corresponding aperture in the wall of the acetabular cup component.

The invention will be understood more fully, while still further objects and advantages will become apparent, in the following detailed description of a preferred embodiment of the invention illustrated in the accompanying drawing, in which.

Figure 1:
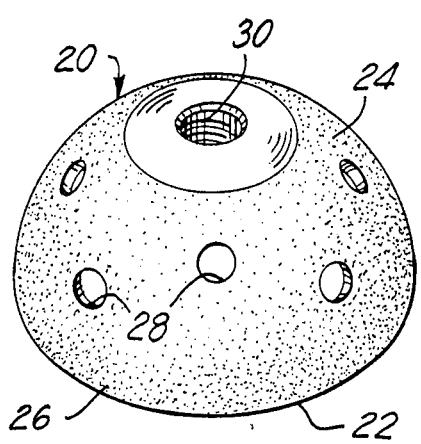
FIG. 1 is a perspective view of an acetabular cup component constructed for cementless affixation.

Referring now to the drawing, and especially to FIG. 1 thereof, an acetabular cup component of a prosthetic hip joint is illustrated at 20 and is seen to include a shell-like wall 22 having an outer surface 24 extending along the exterior of the acetabular cup component 20. A surface treatment 26 is provided along the outer surface 24 for promoting affixation to the natural bone of the hip upon implant, without the use of cement, in a manner now well known in the art of prosthetic implants. A plurality of apertures 28 pass through the wall 22 at spaced apart locations, and a threaded hole 30 is provided at the top of the acetabular cup component 20, all for purposes which will be described below.

Figure 2:
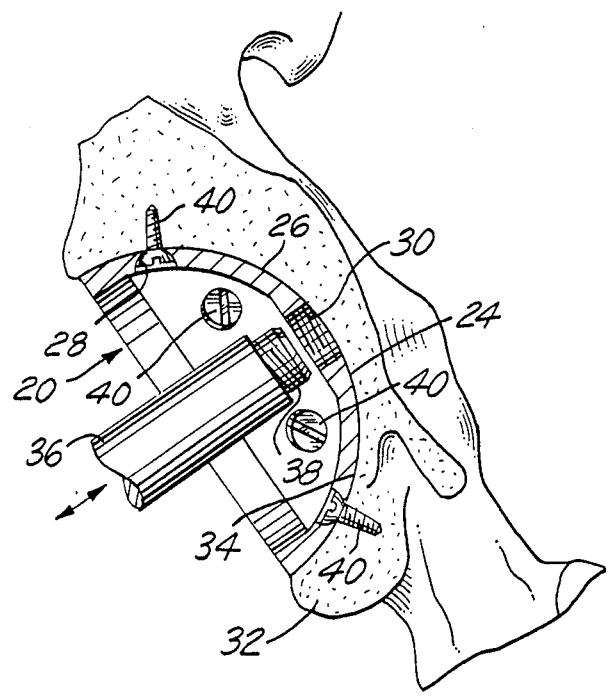
FIG. 2 is a cross-sectional view showing the acetabular cup component implanted in a hip bone, employing conventional cementless affixation.

Turning now to FIG. 2, the acetabular cup component 20 is to be implanted in the acetabulum 32 to provide a suitable site for a bearing component (not shown) of the prosthetic hip joint. The natural bone of the acetabulum 32 has been prepared by establishing a recess 34 complementary to the outer surface 24 of the acetabular cup component 20 so that the cup component 20 may be seated within the recess 34 with the outer surface 24 in intimate contact with the recess 34. Proper placement and orientation of the cup component 20 is facilitated by the attachment of a manipulating instrument 36 to the cup component 20 by means of a threaded post 38 on the instrument 36 brought into engagement with the threaded hole 30. Once the cup component 20 is appropriately seated within the bone at the recess 34, supplemental anchoring screws 40 are inserted, at least through some of the apertures 28, and threaded into the bone of the acetabulum 32 to secure the cup component 20 in place. Affixation of the cup component 20 will be complete upon the growth of bone tissue into cooperation with the surface treatment 26 to secure the cup component 20 in place. Such affixation is accomplished without cement and is referred to as a cementless affixation.

Figure 3:
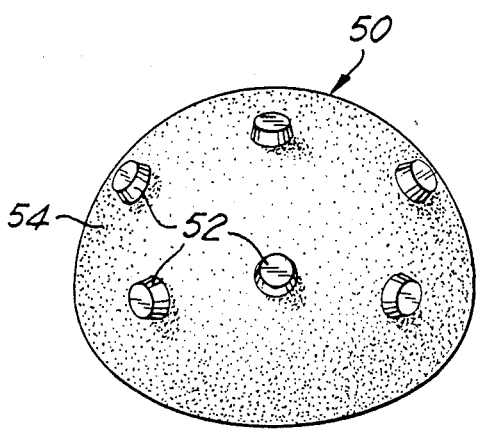
FIG. 3 is a perspective view of an acetabular cup component constructed for cemented affixation.
Figure 4:
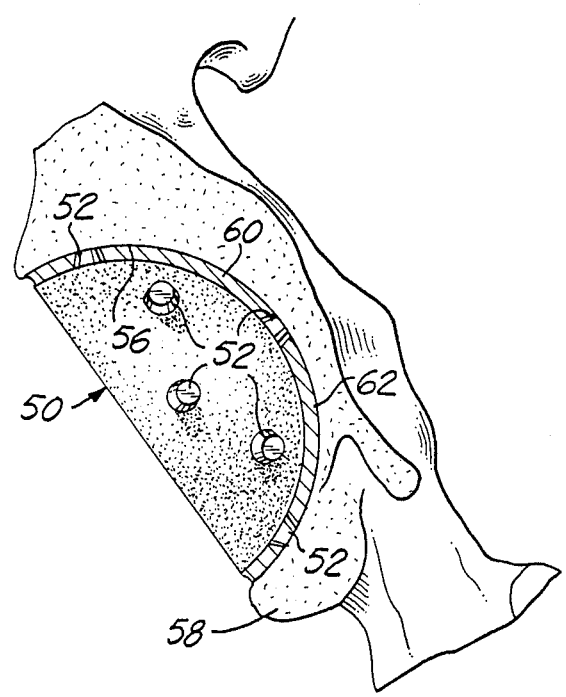
FIG. 4 is a cross-sectional view showing the acetabular cup component of FIG. 3 implanted in a hip bone, employing conventional cemented affixation.

While cementless affixation often is the preferred method of affixation, conditions at the implant site sometimes dictate the use of a cemented affixation. As seen in FIGS. 3 and 4, an acetabular cup component 50 is constructed for cemented affixation and includes a plurality of spacers 52 projecting from the outer surface 54 of the cup component 50. Upon seating of the cup component 50 within a recess 56 prepared in the acetabulum 58, the spacers 52 rest against the bone of the acetabulum 58 and maintain a gap 60 within which a layer 62 of cement secures the cup component 50 in place. Since the length of the spacers 52 is fixed, the depth of the gap 60 is made certain and the thickness of the layer 62 is determined with accuracy, all as is now well known.

Ordinarily, the surgeon will choose the method of affixation prior to commencement of the implant procedure and will the select the appropriate acetabular cup component for the chosen method. However, until the surgeon can examine the site directly, there may be some uncertainty as to the most appropriate means for affixation of the acetabular cup component. Since direct examination of the site is available only after the implant procedure is in progress, deferment of the choice of affixation method until direct examination is accomplished requires that the surgeon have on hand in the operating room or nearby both types of acetabular cup components; that is, the surgeon must be able to select the appropriate cup component immediately so that the procedure may continue without delay. Such a requirement increases the inventory of cup components and related systems which must be on hand and leads to waste and added expense.

The present invention provides a cement spacer system which enables the acetabular cup component 20, constructed for cementless affixation, to be converted for cemented affixation quickly and easily so that conversion can be accomplished, as required, within the operating room, during the implant procedure. Thus, in instances where the surgeon initially has selected the preferred cementless affixation and then subsequently, upon direct examination, during the implant procedure, determines that cemented affixation is better suited to the particular site, conversion of the selected acetabular cup component is available so that the selected cup component may be implanted with cemented affixation, without the requirement for another cup component.

Figure 5:
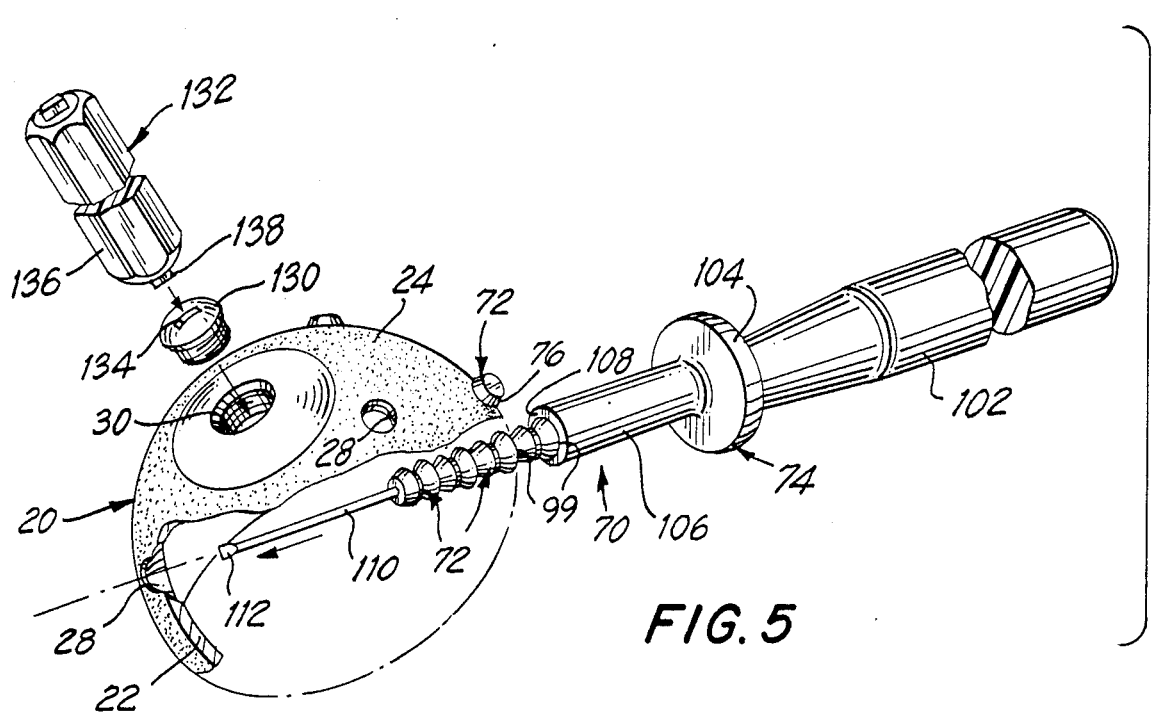
FIG. 5 is a perspective view of a system constructed in accordance with the present invention.
Figure 6:
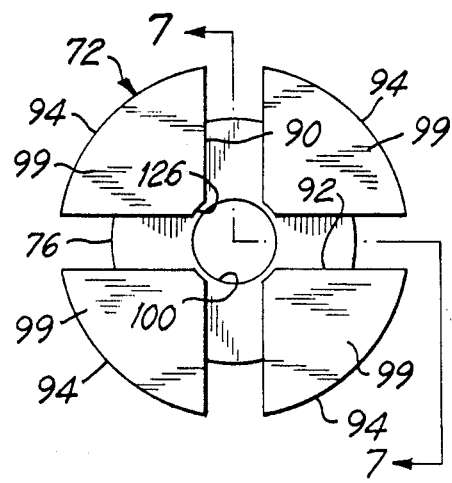
FIG. 6 is a bottom plan view of a cement spacer of the system.
Figure 7:
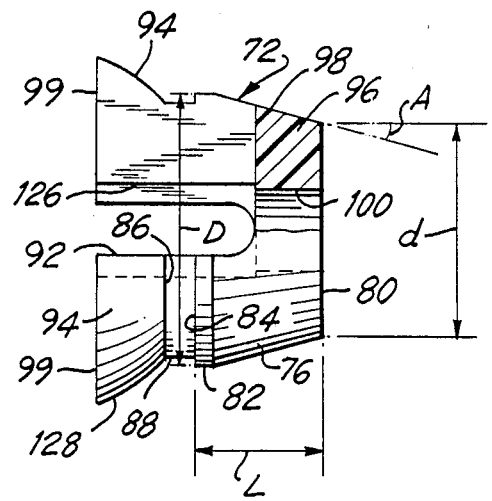
FIG. 7 is a partial cross-sectional view taken along line 7—7 of FIG. 6.

Referring now to FIG. 5, acetabular cup component 20 is seen in the process of conversion from the type of component which is affixed without cement to one for affixation with cement, through the use of a cement spacer system 70 constructed in accordance with the invention. Cement spacer system 70 includes a plurality of cement spacers 72 and a spacer inserter 74. Turning now to FIGS. 6 and 7, as well as to FIG. 5, each cement spacer 72 includes a spacer head 76 having a generally cylindrical configuration and an axial spacing length L between the top 80 and the bottom 82 of the spacer head 76. Confronting locking shoulders 84 and 86 are located adjacent the bottom 82 of the spacer head 76 and are spaced apart axially to establish a groove 88 interposed between the confronting locking shoulders 84 and 86. Mutually perpendicular slots 90 and 92 divide the lower portion of the cement spacer 72 into cantilever sections 94 which depend axially from an upper generally cylindrical portion 96 of the spacer head 76 and which carry the confronting locking shoulders 84 and 86, and the interposed groove 88. The spacer head 76 is provided with a tapered outer peripheral surface 98, the taper extending downwardly and outwardly from a smaller diameter d at the top 80 of the spacer head 76 to a larger diameter D at the bottom 82 of the spacer head 76, the taper preferably making an angle A of about 15° with the axial direction. The slots 90 and 92 extend axially into the spacer head 76 so that the tapered outer peripheral surface 98 extends along the cantilever sections 94. The lower portion of the cement spacer 72 then flares outwardly to a lowermost transverse face 99 of even greater diameter. A central bore 100 passes axially through the cement spacer 72 and renders the overall configuration of the cement spacer 72 generally annular.

The spacer inserter 74 has a gripping handle 102 including a collar 104 placed intermediate the gripping handle 102 and a short shaft 106 having a lateral pushing surface 108 at one end thereof. A locator rod 110 is anchored in the shaft 106 and projects axially beyond the lateral pushing surface 108 to a remote tip 112. The nominal diameter of the locator rod 110 is complementary to the diameter of the bore 100 in the cement spacers 72 and the length of the locator rod 110 is such that the cement spacers 72 may be strung along the locator rod 110, as shown in FIG. 5, with the cement spacers 72 being readily slidable along the length of the locator rod 110. The remote tip 112 of the locator rod 110 is provided with a diameter slightly larger than the remainder of the locator rod 110, and slightly larger than the portion of bore 100 in the spacer head 76 of each cement spacer 72, so that the enlarged tip 112 serves as a detent means for retaining the cement spacers 72 strung upon the locator rod 110. All of the cement spacers 72 are oriented with the lowermost transverse face 99 of each cement spacer 72 facing the lateral pushing surface 108 of the spacer inserter 74.

Figure 8:
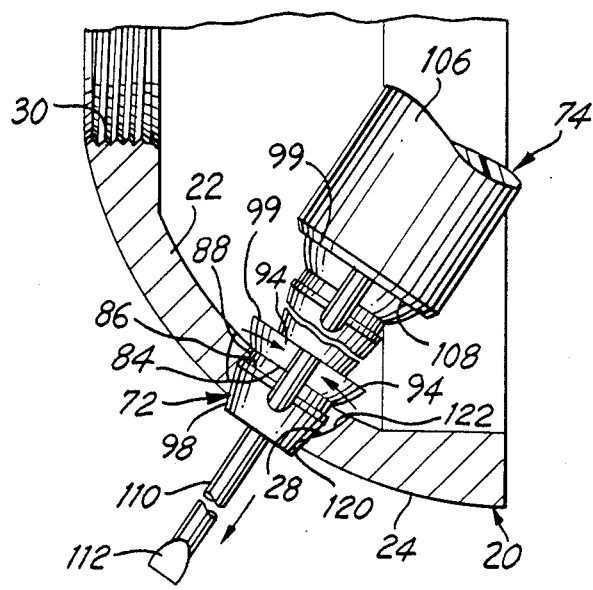
FIG. 8 is an enlarged fragmentary cross-sectional view of a portion of the acetabular cup component illustrating the insertion of a cement spacer.
Figure 9:
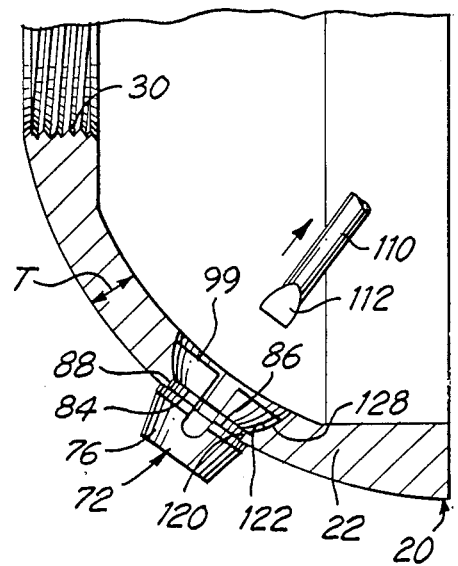
FIG. 9 is a fragmentary view similar to FIG. 8, with the cement spacer fully inserted.

Acetabular cup component 20 is converted selectively for cemented affixation by inserting cement spacers 72 into at least some and preferably all of the existing apertures 28 and securing the inserted cement spacers in place. As best seen in FIGS. 8 and 9, each aperture 28 includes a rim-like portion 120 placed between the outer surface 24 of the acetabular cup component 20 and a countersink 122 provided at the inner surface 124 of the acetabular cup component 20. The relative dimensions of the rim-like portion 120 of each aperture 28 and the confronting locking shoulders 84 and 86, and interposed groove 88 of each cement spacer 72 are such that upon pushing of a cement spacer 72, into a corresponding aperture 28, from the inside of the acetabular cup component 20 toward the outside of the cup component 20 as illustrated in FIGS. 8 and 9, the rim-like portion 120 will engage the tapered outer peripheral surface 98 of the spacer head 76 and the resilient deflection means provided by the tapered outer peripheral surface 98 and the cantilever sections 94 will effect resilient deflection of the cantilever sections 94 laterally inwardly until the upper locking shoulder 84 passes over the rim-like portion 120. Sufficient clearance is provided along the portion 126 of bore 100, which portion 126 passes through the lower portion 128 of the cement spacer 72, to enable the aforesaid deflection of cantilever sections 94. The cantilever sections 94 then will return toward the undeflected condition to capture the rim-like portion 120 within the groove 88, between the confronting locking shoulders 84 and 86, thereby securing the cement spacer 72 in place within the aperture 28. In accomplishing the insertion of each cement spacer 72, the locator rod 110 of the spacer inserter 74 merely is inserted through a selected aperture 28 to bring the cement spacer 72 which is nearest the remote tip 112 of the locator rod 110 to the rim-like portion 120 of the aperture 28. Then a pushing force is exerted on the gripping handle 102 of the spacer inserter 74, which pushing force is transmitted through the strung cement spacers 72 to the cement spacer 72 being inserted, until insertion is accomplished as outlined above. Cement spacers 72 are constructed of a biocompatible material, and preferably are molded of a synthetic resin material which provides the required degree of strength and resilience, one such material being polymethylmethacrylate (PMMA).

It is noted that the overall length of the cement spacer 72 is no greater than the sum of the length L of the spacer head 76 and the thickness T of the wall 22 of the acetabular cup component 20, so that the cement spacers 72 will not intrude into the interior of the cup component 20 and interfere with the specified function of the cup component 20. The flared lower portion 128 of the cement spacer 72 preferably is made complementary to the existing countersink 122 for enhanced security and optimum functioning of the cement spacer 72, subsequent to installation. At the same time, the flared configuration maximizes the area of the transverse face 99 for better distribution of the forces exerted on the cement spacers 72 during insertion.

Figure 10:
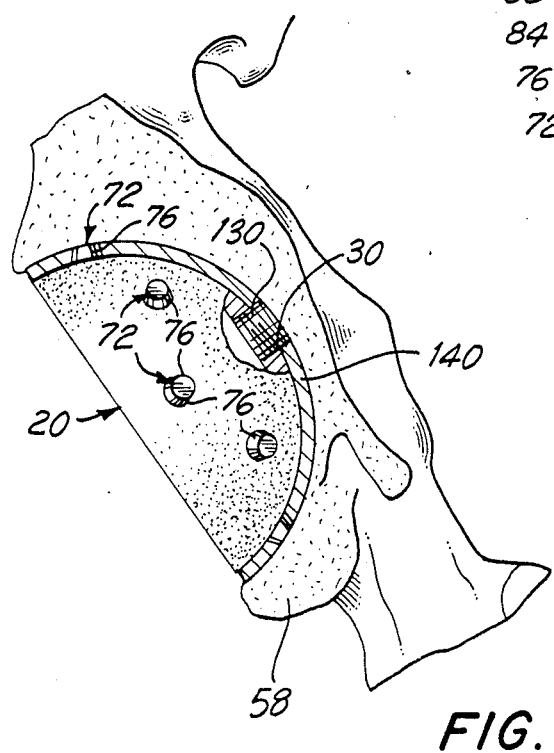
FIG. 10 is a cross-sectional view showing a converted acetabular cup component implanted in a hip bone, employing a cemented affixation.

Conversion of the acetabular cup component 20 is accomplished by the insertion of a plurality of cement spacers 72, and is completed by closing the threaded hole 30. Returning now to FIG. 5, threaded hole 30 is closed with a threaded plug 130 utilizing a wrenching tool 132, all furnished with the system 70. Threaded plug 130 is complementary to threaded hole 30 and includes a wrenching recess 134. Wrenching tool 132 has a handle 136 and a wrenching projection 138 complementary to the wrenching recess 134 so that the wrenching tool 132 is engaged with the threaded plug 130 for threading the threaded plug 130 into the threaded hole 30 and closing the hole 30. Upon implant of the converted acetabular cup component 20, the spacer length L of the spacer heads 76 of the inserted cement spacers 72 provides the necessary spacing for the appropriate cement layer 140, as illustrated in FIG. 10, and the threaded hole 30 is closed against the intrusion of cement into the threaded hole 30.

Figure 11:
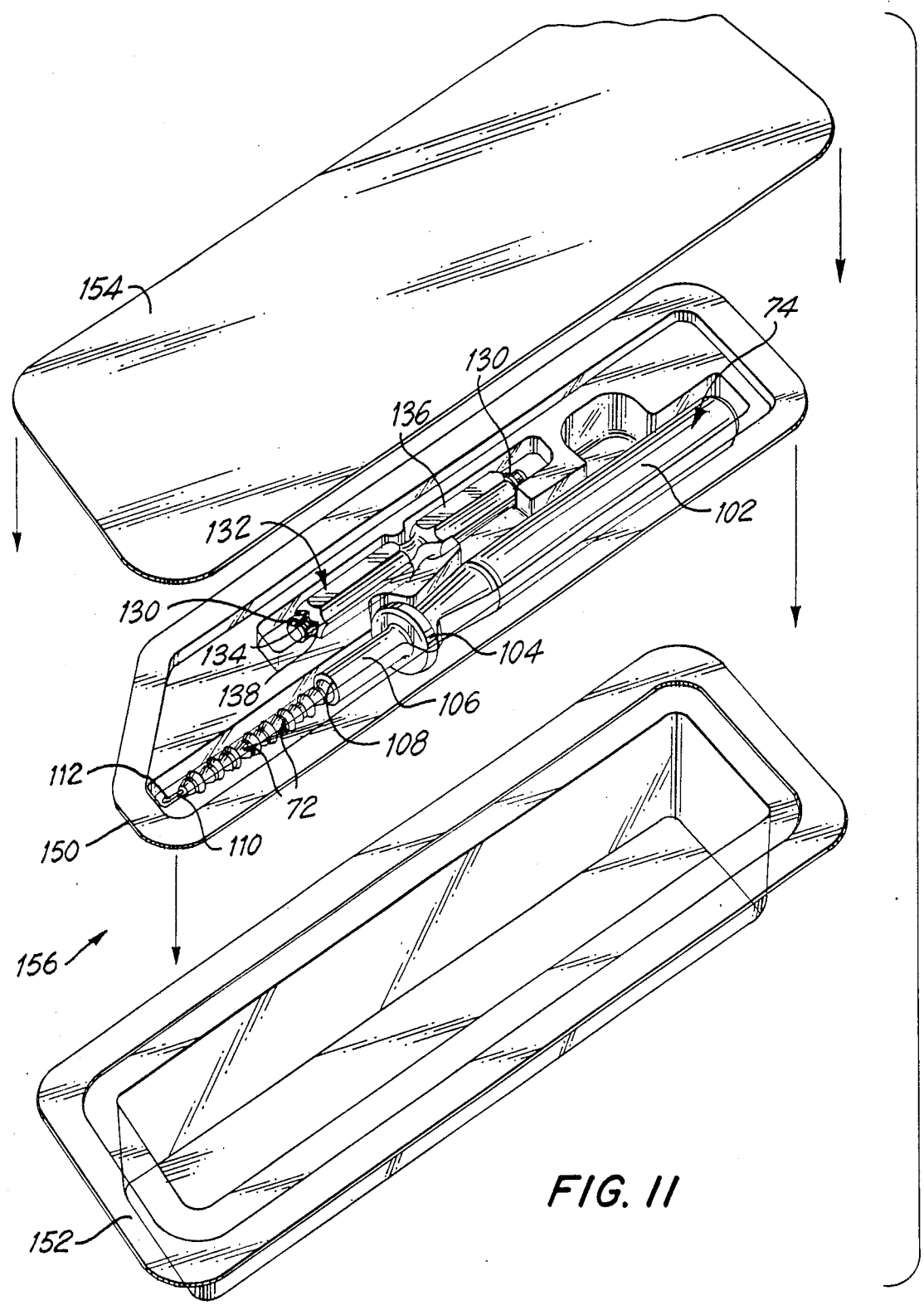
FIG. 11 is an exploded perspective view of a kit containing the system of the present invention.

Cement spacer system 70 is packaged in a kit for convenient use and ready disposal. Thus, as seen in FIG. 11, a sterile tray 150 carries the spacer inserter 74, with the cement spacers 72 strung thereon, and the wrenching tool 132, with the wrenching elements, in the form of projection 138 of the wrenching tool 132 and recess 134 of the threaded plug 130, already engaged. The sterile tray 150 is placed in an outer envelope 152 and the envelope 152 is sealed with a cover 154 to establish a package 156, all in a manner now well known in the packaging of sterile items to be brought into the sterile environment of an operating room. Should a surgeon decide to convert a previously-selected acetabular cup component 20 from a cementless affixation configuration to a cemented affixation configuration, such conversion is accomplished quickly and easily, interoperatively, by merely opening the package 156 and carrying out the above-described conversion procedure, utilizing the already-selected acetabular cup component 20. Preferably, the spacer inserter 74 is a relatively inexpensive construction, the gripping handle 102 being economically molded of a synthetic resin material suitable for the use, and the locator rod 110 preferably being of stainless steel, embedded in the material of the handle 102. Likewise, the wrenching tool 132 is molded of plastic and is expendable. Thus, both the spacer inserter 74 and the wrenching tool 132 are readily disposed of subsequent to use. Preferably, an excess number of cement spacers 72 is supplied in the kit, already strung upon the spacer inserter 74, to assure that an adequate number of cement spacers 72 always is available for completion of a conversion without interruption. Likewise, wrenching tool 132 preferably is double-ended, that is, a wrenching projection 138 preferably is provided at both ends of the wrenching tool 132 so that a threaded plug 130 is engaged with the wrenching tool 132 at each end of the tool, thereby providing a spare threaded plug 130, ready for immediate use, if necessary.

It will be seen that the present invention provides a system which enables a single chosen acetabular cup component of essentially conventional configuration to be affixed either with or without cement so that a surgeon may select the method of affixation interoperatively, without the necessity for having available multiple acetabular cup components during the actual implant procedure and accomplishes the several objects and advantages summarized above; namely, simplifies the procedure and reduces the time necessary for accomplishing the implant of an acetabular cup component, while reducing the cost, in that a single selected acetabular cup component may be implanted with either cementless or cemented affixation, with the choice being made available during the actual implant procedure, enables selection of the most appropriate affixation mechanism interoperatively so as to assure that the preferred mechanism is utilized for maximum effectiveness at reduced risk and at lessened expense, reduces hospital inventory and simplifies preoperative selection of an appropriate acetabular cup component, enhances patient safety and comfort in that optimum affixation is made available with reduced risk, and provides the surgeon with the ability to optimize the implant of a prosthetic hip joint with less time and with increased ease.

It is to be understood that the above detailed description of a preferred embodiment of the invention is provided by way of example only. Various details of design and construction may be modified without departing from the true spirit and scope of the invention as set forth in the appended claims.

The embodiments of the invention in which an exclusive property of privilege is claimed are defined as follows:

1. A cement spacer system for use in combination with an acetabular cup component of the type which includes a shell-like wall having a given wall thickness and an outer affixation surface adapted for direct affixation of the acetabular cup component to the acetabulum and apertures passing through the wall at spaced locations along the outer affixation surface, each aperture defining an inner rim of predetermined inside diameter, for enabling selective interoperative conversion of the acetabular cup component for cemented affixation of the acetabular cup component to the acetabulum, the cement spacer system comprising:

a plurality of cement spacers, each cement spacer including a bore extending axially therethrough, and a spacer head having an axial spacing length, and confronting locking shoulders adjacent the spacer head and having an overall diameter greater than the inside diameter of the rim of a respective aperture in the wall of the acetabular cup component, a generally annular groove essentially complementary to the inside diameter of the rim of the corresponding aperture and interposed between the confronting locking shoulders, and resilient deflection means for enabling lateral resilient deflection of the locking shoulders to admit the rim of the corresponding aperture between the confronting locking shoulders in response to axial insertion of the cement spacer into the respective aperture; and a spacer inserted for use in the selective insertion of the cement spacers into the wall of the acetabular cup component, the spacer inserter including a gripping handle, a locator rod extending axially form the handle and having a rod diameter complementary to the axial bore of each cement spacer such that the cement spacers may be disposed along the locator rod, a lateral pushing surface interposed between the handle and the locator rod and adapted for engaging the confronting adjacent cement spacer disposed along the locator rod whereby axial pushing of the handle transmit axial force to the cement spacers disposed along the locator rod, allowing selective insertion and securement of each cement spacer within a corresponding aperture in the wall of the acetabular cup component.

2. The invention of claim 1 wherein the locator rod extends from the lateral pushing surface to a tip opposite and remote from the pushing surface, the tip having a diameter slightly larger than the axial bore for retaining the cement spacers upon the locator rod and subsequent selective release of each consecutive inserted cement spacer in response to the securement of the inserted cement spacer in the corresponding aperture in the wall of the acetabular cup component.

3. The invention of claim 1 wherein the spacer head of each cement spacer includes an essentially annular portion having a diameter smaller than the inside diameter of the rim of each aperture in the wall of the acetabular cup component, and the resilient deflection means comprises individual cantilever sections extending axially from the essentially annular portion, the confronting locking shoulders of each cement spacer being located on the cantilever sections, the cantilever sections being resiliently deflectable laterally inwardly in response to axial insertion of the cement spacer into a corresponding aperture in the wall of the acetabular cup component.

4. The invention of claim 3 wherein each spacer head includes an outer peripheral surface on the spacer head, the outer peripheral surface being tapered form the smaller diameter annular portion toward the greater overall diameter of the confronting locking shoulders for engagement with the rim of a corresponding aperture to effect deflection of the cantilever sections laterally inwardly in response to axial insertion of the cement spacer into the corresponding aperture in the wall of the acetabular cup component.

5. The invention of claim 1 wherein the cement spacers each have an overall axial length no greater than the sum of the spacing length and the wall thickness of the shell-like wall of the acetabular cup component.

6. A cement spacer system for use in combination with an acetabular cup component of the type which includes a shell-like wall having a given wall thickness and an outer affixation surface adapted for direct affixation of the acetabular cup component to the acetabulum and apertures passing through the wall at spaced locations along the outer affixation surface, each aperture defining an inner rim of prescribed inside diameter, for enabling selective interoperative conversion of the acetabular cup component for cemented affixation of the acetabular cup component to the acetabulum, the cement spacer system comprising:

a plurality of cement spacers, each cement spacer including a spacer head having an axial spacing length, confronting locking shoulders adjacent the spacer head and having an overall diameter greater than the inside diameter of the rim of a respective aperture in the wall of the acetabular cup component, a generally annular groove essentially complementary to the inside diameter of the corresponding aperture and interposed between the confronting locking shoulders, and resilient deflection means juxtaposed with the confronting locking shoulders for enabling lateral resilient deflection of the locking shoulders to admit the rim of the corresponding aperture between the confronting locking shoulders in response to axial insertion of the cement spacer into the respective aperture for effecting selective securement of each cement spacer within a corresponding aperture in the wall of the acetabular cup component.

7. The invention of claim 6 wherein the spacer head of each cement spacer includes an essentially cylindrical portion having a diameter smaller than the inside diameter of the rim of each aperture in the wall of the acetabular cup component, and the resilient deflection means comprises individual cantilever sections extending axially from the cylindrical portion, the confronting locking shoulders of each cement spacer being located on the cantilever sections, the cantilever sections being resiliently deflectable laterally inwardly in response to axial insertion of the cement spacer into a corresponding aperture in the wall of the acetabular cup component.

8. The invention of claim 7 wherein each spacer head includes an outer peripheral surface on the spacer head, the outer peripheral surface being tapered from the smaller diameter cylindrical portion toward the greater overall diameter of the confronting locking shoulders for engagement with the rim of a corresponding aperture to effect deflection of the cantilever sections laterally inwardly in response to axial insertion of the cement spacer into the corresponding aperture in the wall of the acetabular cup component.

9. The invention of claim 6 wherein the cement spacers each have an overall axial length no greater than the sum of the spacing length and the wall thickness of the shell-like wall of the acetabular component.

* * * * *